United States Patent [19]

Chauvin et al.

[11] Patent Number: 5,104,840
[45] Date of Patent: Apr. 14, 1992

[54] NON-AQUEOUS LIQUID COMPOSITION WITH AN IONIC CHARACTER AND ITS USE AS A SOLVENT

[75] Inventors: Yves Chauvin, Le Pecq; Dominique Commereuc, Meudon; Isabelle Guibard, Rueil Malmaison; André Hirschauer, Montesson; Héléne Olivier, Rueil Malmaison; Lucien Saussine, Croissy sur Seine, all of France

[73] Assignee: Institut Francais du Petrole, Rueil Malmaison, France

[21] Appl. No.: 672,236

[22] Filed: Mar. 20, 1991

[30] Foreign Application Priority Data

Mar. 20, 1990 [FR] France ............... 90 03651

[51] Int. Cl.$^5$ .................. B01J 31/22; B01J 31/24; C07C 2/04; C07C 2/24
[52] U.S. Cl. ................... 502/117; 585/502; 585/510; 585/531
[58] Field of Search ............... 585/531, 512, 513, 511; 502/117

[56] References Cited

U.S. PATENT DOCUMENTS

| | | | |
|---|---|---|---|
| 3,418,216 | 12/1968 | Dotzer | 204/14 |
| 3,558,519 | 1/1971 | Phung et al. | 502/117 |
| 4,283,305 | 8/1981 | Chauvin et al. | 502/117 |
| 4,816,610 | 3/1989 | Koskimies et al. | 502/117 |
| 4,992,610 | 2/1991 | Sato et al. | 502/117 |

FOREIGN PATENT DOCUMENTS

0020289 8/1965 Japan .

OTHER PUBLICATIONS

Cohon E. Wiclinson "Advanced Inorganic Chemistry" p. 801, John Wiley Publishers, 1972.

Primary Examiner—Asok Pal
Assistant Examiner—P. Achutamurthy
Attorney, Agent, or Firm—Millen, White & Zelano

[57] ABSTRACT

A non-aqueous liquid composition with an ionic character resulting from the contacting of at least one alkylaluminum dihalide with at least one quaternary ammonium halide and/or at least one quaternary phosphonium halide, said composition being liquid below 80° C., for example, between −70° and +40° C., is useful as a solvent of catalysts for the dimerization, codimerization and oligomerization of olefins.

35 Claims, No Drawings

NON-AQUEOUS LIQUID COMPOSITION WITH AN IONIC CHARACTER AND ITS USE AS A SOLVENT

BACKGROUND OF THE INVENTION

The present invention relates to a non aqueous liquid composition with an ionic character resulting from the contacting of at least one alkylaluminum dihalide with at least one quaternary ammonium halide or/and at least one quaternary phosphonium halide, said composition being liquid below about 80° C. and preferably at temperatures lower than or equal to about 40° C..

The object of the present invention is also the use of said liquid composition as a solvent (notably for catalysts).

Only few non aqueous ionic compositions which are liquid below the room temperature and one constituent of which is soluble in aliphatic hydrocarbons are known. Those which have been studied most are formed by the mixing of aluminum trichloride or tribromide with N-alkylpyridinium and N,N'-dialkyl imidazolium chlorides or bromides. These liquid ionic compositions are called "molten salts" (C. H.. HUSSEY, Advances in Molten Salts Chemistry, Vol.5, p.185, Elsevier, New-York, 1983).

The use of these molten salts as solvents and cocatalysts for the dimerization or codimerization reaction of olefins catalyzed by nickel cationic complexes comprising a nickel-carbon or a nickel-hydrogen bond has also been described in French patent 2,611,700.

It has now been discovered that the contacting (in any order) of at least one alkylaluminum dihalide (for example a dichloride or a dibromide) with at least one quaternary ammonium halide (for example a chloride or a bromide) or/and at least one quaternary phosphonium halide (for example a chloride or a bromide) and also possibly with at least one aluminum trihalide (for example an aluminum trichloride or tribromide) leads to a non aqueous liquid composition with an ionic character, said composition being liquid below about 80° C. (for example between about −70° C. and about +80° C.), preferably at temperatures lower than or equal to about 40° C. (for example between about −70° C. and about +40° C.) and, more preferably, at temperatures lower than or equal to about −20° C. (for example between about −70° C. and about −20° C.). Besides, said liquid composition is stable with respect to time.

DETAILED DESCRIPTION OF THE INVENTION

The alkylaluminum dihalides that can be used within the scope of the invention preferably correspond to the general formula $Al_2X_4R_2$, where each X represents a halogen, selected for example from chlorine and bromine, each R represents a hydrocarbyl remainder comprising 1 to 12 atoms of carbon, aromatic or aliphatic, with a branched or a linear chain. As examples of such compounds, dichloromethylaluminum (common name of tetrachlorodimethyl-dialuminum of formula $Al_2Cl_4(CH_3)_2$), dibromomethylaluminum $(Al_2Br_4(CH_3)_2)$, dichloroethylaluminum, dibromoethyl-aluminum, dichloro n-hexylaluminum, dichloroisobutylaluminum can be cited. One or several of these compounds can be used.

The quaternary ammonium halides and the quaternary phosphonium halides which can be utilized within the scope of the invention preferably correspond to the respective general formulas $NR_1R_2R_3R_4X$ and $PR_1P_2P_3P_4X$, where X represents a halogen, selected for example from chlorine and bromine, $R_1$, $R_2$, $R_3$ and $R_4$, identical or different, representing each an alkyl group, aliphatic (saturated or unsaturated) or aromatic, comprising 1 to 12 atoms of carbon. These groups $R_1$, $R_2$, $R_3$ and $R_4$ can also form a cycle with the atom of nitrogen or of phosphorus; thus, $R_1$ and $R_2$ can form together an alkylene remainder with 4 to 10 atoms of carbon, $R_3$ and $R_4$ being defined as previously. The ammonium halides and the phosphonium halides can be formed by at least one nitrogenated or phosphorated heterocycle comprising 1, 2 or 3 atoms of nitrogen or of phosphorus. As examples of ammonium or phosphonium halides, tetrabutylphosphonium chloride, tetrabutylphosphonium bromide, N-butylpyridinium chloride, ethylpyridinium bromide, 1-methyl chloride 3-butyl imidazolium, 1-methyl chloride 3-ethyl imidazolium can be cited. One or several of these compounds can be utilized.

The compounds going into the composition according to the invention can be mixed in any order. The mixing can be performed by a simple contacting of said compounds, followed by stirring, until a homogenous liquid phase is obtained (that is to say the liquid composition according to the invention). The mixing can also be advantageously carried out in the presence of a saturated aliphatic hydrocarbonated solvent which dissolves for example the alkylaluminum dihalide(s); in this case, after obtaining two limpid liquid phases, the supernatant phase mainly consisting of the hydrocarbonated solvent is removed so that only the liquid composition according to the invention remains.

The relative proportions of the compounds going into the composition according to the invention depend on the properties, both chemical and physical, which are wanted for the composition according to the invention. When the number $N_1$ of the moles of alkylaluminum dihalide(s), and possibly of aluminium trihalide(s), counted in atoms of aluminium equivalents, equals the number $N_2$ of moles of quaternary ammonium halide(s) or/and quaternary phosphonium halide(s), counted in atoms of halides equivalents, the obtained liquid composition is called "neutral"; if $N_1$ is higher than $N_2$, the obtained liquid composition is called "acid"; if $N_1$ is smaller than $N_2$, the obtained liquid composition is called "basic".

The liquid compositions (or "molten salts") according to the present invention can be used as solvents (notably for catalysts).

It is thus possible to dissolve in these "molten salts" cationic complexes of transition metals, such as $\partial Cr(C_6H_5)_2[^+$, $\partial Re(CO)_5(NS)[^{2+}$, $\partial Fe(fulvene)_2[^{2+}$, $\partial Ru(CH_3CN)_3(C_6H_6)[^{2+}$, $\partial Ru(grit)[^{2+}$, $\partial(C_5H_5)Rh(C_6H_6)[^{2+}$, anionic complexes, such as $\partial NiCl_4[^{2-}$; $\partial NiBr_3P(C_6H_5)_3[^-$, neutral complexes, such as $Ni(C_5H_7O_2)_2$ (nickel acetylacetonate), $(NiCl_2\cdot 2\text{-}PBu_3)$. The neutral complexes can then also be converted into complexes with an ionic character in the basic "molten salts" and of a cationic character in the acid "molten salts"; the nickel acetylacetonate introduced into the liquid basic "molten salt" consisting of 1 mole of 1-methyl chloride 3-butyl imidazolium and 0.9 mole of dichlorethylaluminum is thus quantitatively converted into a $[NiCl_4]^{2-}$ complex.

The liquid compositions (or "molten salts") according to the invention can also be used as solvents for catalysts, for example catalysts based on complexes of transition metals, notably for dimerization, codimerization or oligomerization reactions, such as nickel complexes. In this case, the use of complexes is no longer limited, as in French patent 2,611,700, to the complexes already comprising at least one transition metal-carbon or transition metal-hydrogen bond, or to complexes with a low degree of oxidation, but to the major part of the complexes.

The catalysts which can thus be used in a liquid composition (or "molten salt") according to the invention for the dimerization, codimerization or oligomerization of olefins are any nickel complexes, except nickel complexes solvated by compounds having active protons such as water, alcohols, organic acids, ammonia. As examples of such complexes for said reactions, nickel acetylacetonate, halide or nickel sulfate complexes such as $(NiCl_2, 2$ pyridine$)$, $(NiCl_2, 2PiPr_3)$, $(NiBr_2, 2PBu_3)$, $(NiSO_4, 2PBu_3)$, nickel octanoate nickel alcoholates can be cited. The nickel compounds described in French patent 2,611,700 can also be used, which comprise at least one nickel-carbon or nickel-hydrogen bond, or which have a valence smaller than 2; as examples of such compounds, nickel biscyclooctadiene, methallylnickel chloride, bisallylnickel, allylnickel chloride, allylnickel bromide can be cited.

The amount of nickel complex(es) contained in the "molten salt" according to the invention, for the dimerization, codimerization or oligomerization of olefins, generally ranges from 0.01 m mole.$l^{-1}$ to 2 moles.$l^{-1}$, preferably from 0.1 to 100 m moles.$l^{-1}$; the optimum proportion depends on the nature of the nickel complex and on the composition of the "molten salt" according to the invention. The "acid" field of the "molten salt" will be preferably considered and the amount of complex will be adjusted to the excess molar fraction of alkylaluminum dihalide(s) contained in the "molten salt".

Generally speaking, the olefins that are likely to be dimerized, codimerized or oligomerized by the catalyst(s) contained in a "molten salt" according to the invention are the same as those which are dimerized by the nickel-based catalysts used in a hydrocarbonated or halogeno-hydrocarbonated medium, for example ethylene, propylene, 1-and 2-butenes, styrene. To perform the reaction, the olefin is contacted with the "molten salt" phase containing the nickel complex(es) and an efficient phase transfer is preferably achieved by means of a strong stirring. At the end of the reaction, the phases are separated by any appropriate means; for example, the mixture is decanted with the upper phase consisting of the dimers, the codimers and/or the oligomers being withdrawn. The operation can then be repeated by introducing a new feedstock of olefin(s). It can also be operated continuously, that is to say by supplying the medium with olefin(s) and continuously withdrawing the phase consisting of the dimers, the codimers and/or the oligomers as they form, while making sure to make, inside or outside the reactor, a zone allowing the decanting of the two liquid phases.

The temperature at which the dimerization, codimerization or oligomerization reaction takes place can be as low as allowed by the composition of the "molten salt" and the catalyst activity, for example $-50°$ C. to $+80°$ C.

The pressure is generally maintained between 0.01 and 10 MPa, high pressures being particularly utilized for ethylene.

As for the nickel catalysts used as purely organic solvents, they are it is usually protected from oxygen and humidity.

The following examples illustrate the invention without however limiting its scope. What will be called "content" of the liquid composition (or "molten salt") is the molar fraction of aluminum compound(s); for example, a liquid composition containing 0.5 mole of aluminum compound(s) for 1 mole of the sum of the constituents of said composition will have a content of 0.5 N.

EXAMPLE 1

Preparation of a liquid composition according to the invention 9.74 g (33 mmoles) of $PBu_4Cl$ (tetrabutylphosphonium chloride) and 15 ml of heptane are introduced into a Schlenk tube free from air and humidity; then, after the suspension has been cooled down to $-20°$ C., 8 ml (6.46 g) of a solution of 50 % by weight of dichloroethylaluminum (i.e. 25.4 milliequivalents of atoms of aluminum) in hexane are added. The obtained mixture is then heated up to about 30° C.

The forming of two limpid liquid phases is then observed, the hydrocarbonated supernatant phase containing no chlorinated compound and being then removed.

The lower homogenous liquid phase consists of a composition which is liquid at the room temperature and which shows a content of 0.43 N.

EXAMPLE 2

Preparation of a liquid composition according to the invention.

8.38 g (48.1 mmoles) of 1-methyl chloride 3-butyl imidazolium are introduced into a Schlenk tube free from air and humidity. Then, after cooling the suspension down to $-20°$ C., 11.8 ml (9.56 g) of a solution of 50 % by weight of dichloroethylaluminum (i.e. 37.6 milliequivalents of atoms of aluminum) in hexane are added. The obtained mixture is then heated up to about 30° C.

The forming of two limpid liquid phases can then be observed.

After removing the hydrocarbonated supernatant phase, a liquid composition with a content of 0.44 N, and which is still liquid at $-30°$ C., is collected.

EXAMPLE 3

Preparation of a liquid composition according to the invention 2.23 g (7.55 mmoles) of $PBu_4Cl$ and 15 ml of heptane are introduced into a Schlenk tube free from air and humidity; then, after cooling the suspension down to $-20°$ C., 2.3 ml (1.84 g) of a solution of 50 % by weight of dichloroethylaluminum (i.e. 7.1 milliequivalents of atoms of aluminum) in hexane are added. The obtained mixture is heated up to about 30° C.

The forming of two limpid liquid phases can then be observed.

After removing the hydrocarbonated supernatant phase, a liquid composition with a content of 0.66 N, and which is still liquid at $+30°$ C., is gathered.

EXAMPLE 4

Preparation of a liquid composition according to the invention 5.1 g (29.3 mmoles) of 1-methyl chloride 3-butyl imidazolium are introduced into a Schlenk tube free from air and humidity. Then, after cooling the suspension down to $-20°$ C., 7 ml (5.65 g) of a solution of 50% by weight of dichloroethylaluminum (i.e. 22.2 milliequivalents of atoms of aluminum) in hexane are added. The obtained mixture is then heated up to about 30° C.

The forming of two limpid liquid phases can then be observed.

After removing the hydrocarbonated supernatant phase, a liquid composition with a content of 0.60 N, and which is still liquid at $-50°$ C., is gathered.

EXAMPLE 5

Dimerization test according to the invention 0.125 g (0.23 mmoles) of the ($NiCl_2,2PBu_3$) complex, 10 g of heptane, then 5 g of a liquid composition consisting of tetrabutyl phosphonium chloride and of dichloroethylaluminum with a content of 0.65 N are introduced into a 250 ml-steel reactor free from air and humidity.

It is then pressurized at 0.5 MPa of propylene and the mixture is brought to about 60° C.

After two hours of stirring, 30 g of propylene oligomers consisting of 85 % of isohexenes are gathered.

EXAMPLE 6

Dimerization test according to the invention 0.26 g (1.0 mmole) of anhydrous nickel acetylacetonate, 9 g of heptane, then 5 g of a liquid composition consisting of 1-methyl chloride 3-butyl imidazolium and of dichloroethylaluminum with a content of 0.64 N are introduced into a 250 ml-steel reactor free from air and humidity.

It is then pressurized at 0.5 MPa of propylene and the mixture is brought to about 60° C.

After two hours of stirring, 9 g of propylene oligomers consisting of 82 % of isohexenes are gathered.

EXAMPLE 7

0.024 millimole of the ($NiCl_2.2Pir_3$) complex, 3 ml of heptane and 2 ml of a molten salt 0.7 N consisting of a mixture of dichloroethylaluminum and of 1-methyl chloride 3-butyl imidazolium are successively introduced into a double-walled glass reactor containing a bar magnet, free from air and humidity and maintained at $-15+$ C. Gaseous dimers have been formed, 76 % of which consisting of 2,3dimethyl butenes.

We claim:

1. A process for dimerizing, codimerizing, or oligomerizing at least one olefin, wherein said olefin is contacted with at least one nickel complex, said complex being present in a non-aqueous liquid composition with an ionic character resulting from the contacting of at least one alkylaluminum dihalide with at least one quaternary ammonium halide and/or at least one quaternary phosphonium halide, said composition being liquid below about 80° C.

2. A process according to claim 1, said non-aqueous ligand composition being liquid at temperatures lower than or equal to about 40° C.

3. A process according to claim 1, said non-aqueous ligand composition being liquid between about $-70°$ C. and about 40° C.

4. A process according to claim 1, said non-aqueous ligand composition being liquid at temperatures lower than or equal to about $-20°$ C.

5. A process according to claim 1, said non-aqueous ligand composition being liquid between about $-70°$ C. and about $-20°$ C.

6. A process according to claim 1, wherein said alkylaluminum dihalide is an alkylaluminum dichloride or dibromide.

7. A process according to claim 1, wherein said alkylaluminum dihalide corresponds to the general formula $Al_2X_4R_2$, where each X represents a halogen selected from chlorine and bromine, and each R represents a hydrocarbyl remainder comprising 1 to 12 atoms of carbon.

8. A process according to claim 7 wherein said alkylaluminum dihalide is selected from the group formed by dichloromethylaluminum, dibromomethylaluminum, dichloroethylaluminum, dibromomethylaluminum, or dichloro n-hexylaluminum, dichloroisobutylaluminum.

9. A process according to claim 1, wherein said quaternary ammonium halide is a quaternary ammonium chloride or bromide and said quaternary phosphonium halide is a quaternary phosphonium chloride or bromide.

10. A process according to claim 1, wherein said quaternary ammonium halide and said quaternary phosphonium halide, respectively, correspond to the general formulae $NR_1R_2R_3R_4X$ and $Pr_1R_2R_3R_4X$, where X represents a halogen selected from chlorine and bromine; $R_1$, $R_2$, $R_3$ and $R_4$, identical or different, each represent an alkyl group comprising 1 to 12 atoms of carbon; and, where $R_1$ and $R_2$ together form an alkylene remainder with 4 to 10 atoms of carbon, $R_3$ and $R_4$, identical or different, each represent an alkyl group comprising 1 to 12 atoms of carbon.

11. A process according to claim 1 wherein said quaternary ammonium halide and said quaternary phosphonium halide are formed by at least one nitrogenated or phosphorated heterocycle comprising 1, 2 or 3 atoms of nitrogen or phosphorus.

12. A process according to claim 1, wherein said quaternary ammonium halide and said quaternary phosphonium halide are selected from the group consisting of tetrabutyl-phosphonium chloride, tetrabutylphosphonium bromide, N-butylpyridinium chloride, ethylpyridinium bromide, 1-methyl chloride 3-butyl imidazolium, and 1-methyl chloride 3-ethyl imidazolium.

13. A process according to claim 1, said contacting being performed in the presence of a saturated aliphatic hydrocarbon solvent.

14. A process according to claim 1, said contacting also being performed with at least one aluminum trihalide.

15. A solution comprising at least one complex of a transition metal, dissolved in a non-aqueous liquid composition with an ionic character resulting from the contacting of at least one alkylaluminum dihalide with at least one quaternary ammonium halide and/or at least one quaternary phosphonium halide, said composition being liquid below about 80° C.

16. A process according to claim 1 wherein said nickel complex comprises neither a nickel-carbon bond, nor a nickel-hydrogen bond.

17. A process according to claim 1 wherein said nickel complex is nickel acetylacetonate, the (NiCl$_2$,2 pyridine) complex, the (NiCl$_2$,2PiBr$_3$) complex, the (NiBr$_2$,2PBu$_3$) complex, the (NiSO$_4$,2PBu$_3$) complex, nickel octanoate, the nickel alcoholates, nickel biscyclooctadiene, methallylnickel chloride, bisallylnickel, allylnickel chloride, or allylnickel bromide.

18. A process according to claim 1 wherein the amount of nickel complex(es) contained in said liquid composition ranges from 0.01 mmole.l$^{-1}$ to 2 moles.l$^{-1}$.

19. A process according to claim 1 wherein said olefin is ethylene, propylene, 1- and or 2-butene, or styrene.

20. A non-aqueous liquid with solution according to claim 15, said with an ionic character resulting from the contacting of at least one alkylaluminum dihalide with at least one quaternary ammonium halide, said composition being liquid below about 80° C.

21. A solution according to claim 15, said said non-aqueous liquid solution being liquid at temperatures lower than or equal to about 40° C.

22. A solution according to claim 15, said non-aqueous liquid solution being liquid between about −70° C. and about +40° C.

23. A solution according to claim 15, said non-aqueous liquid solution being liquid at temperatures lower than or equal to about −20° C.

24. A solution according to claim 15, said non-aqueous liquid solution being liquid between about −70° C. and about −20° C.

25. A solution according to claim 15, said alkylaluminum dihalide is an alkylaluminum dichloride or dibromide.

26. A solution according to claim 15, wherein said alkylaluminum dihalide corresponds to the general formula Al$_2$X$_4$R$_2$, where each X represents a halogen selected from chlorine or bromine, and each R represents a hydrocarbyl remainder comprising 1 to 12 atoms of carbon.

27. A solution according to claim 16, wherein said alkylaluminum dihalide is dichloromethylaluminum, dibromo-methylaluminum, dichlorethylaluminum, dibromomethylaluminum, dichloro-n-hexyl-aluminum, or dichloroisobutylaluminum.

28. A solution according to claim 15, wherein said quaternary halide is a quaternary ammonium chloride or bromide, and said quaternary phosphonium halide is a quaternary phosphonium chloride or bromide.

29. A solution according to claim 15, wherein said quaternary ammonium halide and said quaternary phosphonium halide, respectively, correspond to the general formulae NR$_1$R$_2$R$_3$R$_4$X and PR$_1$R$_2$R$_3$R$_4$X, where X represents a halogen selected from chlorine and bromine; R$_1$, and R$_2$, R$_3$ and R$_4$, identical or different, each represent an alkyl group comprising 1 to 12 atoms of carbon; and, where R$_1$ and R$_2$ together form an alkylene remainder with 4 to 10 atoms of carbon, R$_3$ and R$_4$, identical or different, each represent an alkyl group comprising 1 to 12 atoms of carbon.

30. A solution according to claim 15, wherein said quaternary ammonium halide and said quaternary phosphonium halide are formed by at least one nitrogenated or phosphorated heterocycle comprising 1, 2 or 3 atoms of nitrogen or phosphorus.

31. A solution according to claim 15, wherein said quaternary ammonium halide and said quaternary phosphonium halide are selected from the group consisting of tetrabutyl-phosphonium chloride, tetrabutylphosphonium bromide, N-butyl-pyridinium chloride, ethylpyridinium bromide, 1-methyl chloride 3-butyl imidazolium, and 1-methyl chloride 3-ethyl imidazolium.

32. A solution according to claim 15, said contacting being performed in the presence of a saturated aliphatic hydrocarbon solvent.

33. A solution according to claim 32, said contacting also being performed with at least one aluminum trihalide.

34. A solution according to claim 15, wherein said transition metal is Cr, Re, Fe, Ru, Rh or Ni.

35. A solution according to claim 15, wherein said transition metal is Ni.

* * * * *